(12) United States Patent
He (10) Patent No.: US 7,939,762 B2
(45) Date of Patent: *May 10, 2011

(54) FEEDTHRU ASSEMBLY

(75) Inventor: Tom Xiaohai He, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 69 days.

This patent is subject to a terminal disclaimer.

(21) Appl. No.: 12/367,080

(22) Filed: Feb. 6, 2009

(65) Prior Publication Data

US 2009/0139765 A1 Jun. 4, 2009

Related U.S. Application Data

(63) Continuation of application No. 11/452,639, filed on Jun. 14, 2006, now Pat. No. 7,498,516.

(51) Int. Cl.
*H01R 4/00* (2006.01)

(52) U.S. Cl. .................................. 174/94 R; 174/94 S (58) Field of Classification Search ............ 174/74 R, 174/76, 77 R, 79, 84 R, 88 R, 94 R
See application file for complete search history.

(56) References Cited

U.S. PATENT DOCUMENTS

| | | | |
|---|---|---|---|
| 2,832,132 A * | 4/1958 | Stineman, Jr. ................ | 228/184 |
| 3,994,430 A | 11/1976 | Cusano et al. | |
| 4,441,777 A * | 4/1984 | Harootion ..................... | 439/274 |
| 4,678,868 A | 7/1987 | Kraska et al. | |
| 4,854,495 A | 8/1989 | Yamamoto et al. | |
| 4,940,858 A * | 7/1990 | Taylor et al. .......... | 174/152 GM |
| 4,991,582 A * | 2/1991 | Byers et al. ....................... | 607/2 |
| 5,013,612 A | 5/1991 | Hunt et al. | |
| 5,028,495 A | 7/1991 | Hirano et al. | |
| 5,046,242 A | 9/1991 | Kuzma et al. | |
| 5,193,539 A | 3/1993 | Schulman et al. | |
| 5,193,540 A | 3/1993 | Schulman et al. | |
| 5,272,283 A | 12/1993 | Kuzma et al. | |
| 5,312,439 A | 5/1994 | Loeb et al. | |

(Continued)

FOREIGN PATENT DOCUMENTS

WO WO-00/56394 9/2000

(Continued)

OTHER PUBLICATIONS

US 5,869,267, 2/1999, Hittmann et al. (withdrawn).*

*Primary Examiner* — William H Mayo, III (74) *Attorney, Agent, or Firm* — Frommer Lawrence & Haug LLP; Bruce E. Black (57) ABSTRACT

A feedthru assembly configured to provide a conductive path extending between an interior of an enclosure and an exterior of the enclosure includes a flange, at least one conductive pin, and at least one insulative member. The flange is configured to couple to the enclosure and has one or more holes therein. The at least one conductive pin includes a hollow lumen extending therethrough and is configured to extend through the at least one or more holes of the flange such that a proximal end of the at least one pin is in communication with the interior of the enclosure and a distal end of the at least one pin is in communication with the exterior of the enclosure. The at least one insulative member is configured to prevent the at least one pin from making physical contact with the flange.

20 Claims, 12 Drawing Sheets

U.S. PATENT DOCUMENTS

| | | | |
|---|---|---|---|
| 5,470,345 A | 11/1995 | Hassler et al. | |
| 5,501,703 A | 3/1996 | Holsheimer et al. | |
| 5,513,793 A | 5/1996 | Malmgren | |
| 5,620,476 A | 4/1997 | Truex et al. | |
| 5,640,764 A | 6/1997 | Strojnik | |
| 5,650,759 A * | 7/1997 | Hittman et al. | 333/182 |
| 5,738,270 A | 4/1998 | Malmgren | |
| 5,750,926 A | 5/1998 | Schulman et al. | |
| 5,782,891 A | 7/1998 | Hassler et al. | |
| 5,811,206 A | 9/1998 | Sunderland et al. | |
| 5,821,011 A | 10/1998 | Taylor et al. | |
| 5,825,608 A * | 10/1998 | Duva et al. | 361/302 |
| 5,843,140 A | 12/1998 | Strojnik | |
| 5,866,851 A * | 2/1999 | Taylor et al. | 174/152 GM |
| 5,867,361 A | 2/1999 | Wolf et al. | |
| 5,870,272 A | 2/1999 | Seifried et al. | |
| 5,871,513 A | 2/1999 | Taylor et al. | |
| 5,896,267 A | 4/1999 | Hittman et al. | |
| 5,905,627 A * | 5/1999 | Brendel et al. | 361/302 |
| 5,938,688 A | 8/1999 | Schiff | |
| 6,016,449 A | 1/2000 | Fischell et al. | |
| 6,031,710 A | 2/2000 | Wolf et al. | |
| 6,043,437 A | 3/2000 | Schulman et al. | |
| 6,051,017 A | 4/2000 | Loeb et al. | |
| 6,052,623 A | 4/2000 | Fenner et al. | |
| 6,061,596 A | 5/2000 | Richmond et al. | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,219,580 B1 | 4/2001 | Faltys et al. | |
| 6,221,513 B1 | 4/2001 | Lasater | |
| 6,259,103 B1 * | 7/2001 | Pressnall | 250/483.1 |
| 6,259,937 B1 | 7/2001 | Schulman et al. | |
| 6,272,382 B1 | 8/2001 | Faltys et al. | |
| 6,280,873 B1 | 8/2001 | Tsukamoto | |
| 6,308,101 B1 | 10/2001 | Faltys et al. | |
| 6,349,025 B1 | 2/2002 | Fraley et al. | |
| 6,381,496 B1 | 4/2002 | Meadows et al. | |
| 6,458,171 B1 | 10/2002 | Tsukamoto | |
| 6,487,446 B1 | 11/2002 | Hill et al. | |
| 6,498,043 B1 | 12/2002 | Schulman et al. | |
| 6,516,227 B1 | 2/2003 | Meadows et al. | |
| 6,516,808 B2 | 2/2003 | Schulman | |
| 6,521,350 B2 | 2/2003 | Fey et al. | |
| 6,529,103 B1 | 3/2003 | Brendel et al. | |
| 6,553,263 B1 | 4/2003 | Meadows et al. | |
| 6,582,441 B1 | 6/2003 | He et al. | |
| 6,586,675 B1 * | 7/2003 | Bealka et al. | 174/50.56 |
| 6,596,439 B1 | 7/2003 | Tsukamoto et al. | |
| 6,605,383 B1 | 8/2003 | Wu | |
| 6,607,843 B2 | 8/2003 | Ruth, II et al. | |
| 6,622,046 B2 | 9/2003 | Fraley et al. | |
| 6,660,116 B2 | 12/2003 | Wolf et al. | |
| 6,736,770 B2 | 5/2004 | Leysieffer et al. | |
| 6,738,672 B2 | 5/2004 | Schulman et al. | |
| 6,760,626 B1 | 7/2004 | Boveja | |
| 6,918,530 B2 | 7/2005 | Shinkai et al. | |
| 6,935,897 B2 | 8/2005 | Canfield et al. | |
| 6,986,453 B2 | 1/2006 | Jiang et al. | |
| 6,989,200 B2 | 1/2006 | Byers et al. | |
| 7,022,415 B2 | 4/2006 | Schnittgrund | |
| 7,046,499 B1 * | 5/2006 | Imani et al. | 361/302 |
| 7,132,173 B2 | 11/2006 | Daulton | |
| 7,437,193 B2 | 10/2008 | Parramon et al. | |
| 2003/0096162 A1 | 5/2003 | Lasater et al. | |
| 2003/0134194 A1 | 7/2003 | Lasater | |
| 2005/0194426 A1 | 9/2005 | Jiang et al. | |
| 2005/0255380 A1 | 11/2005 | Lasater et al. | |

FOREIGN PATENT DOCUMENTS

| | | |
|---|---|---|
| WO | WO-00/56677 | 9/2000 |
| WO | WO-01/24962 | 4/2001 |

* cited by examiner

FEEDTHRU ASSEMBLY

CROSS-REFERENCE TO RELATED APPLICATION

The present application is a Continuation of U.S. patent application Ser. No. 11/452,639, filed Jun. 14, 2006, which is incorporated herein by reference in its entirety

BACKGROUND

A wide variety of medical conditions and disorders have been successfully treated using implantable medical devices. Such implantable devices include, but are not limited to, stimulators, pacemakers, and defibrillators. Implantable devices are often housed within hermetically sealed enclosures configured to exclude water vapor but permit passage of electromagnetic fields used to transmit data and/or power.

It is often desirable to electrically couple an implantable medical device to another device. For example, an implantable device may be coupled to a lead having a number of electrodes disposed thereon so that the device may deliver electrical stimulation to a site within the body. Alternatively, an implantable device may be electrically coupled to an external device configured to communicate with and support the implantable device.

To facilitate electrical coupling to another device, many implantable devices include one or more electrical feedthru assemblies. Electrical feedthru assemblies provide a conductive path extending between the interior of a device's enclosure and a point outside the enclosure. A common type of feedthru assembly includes an array of conductive pins that have been connected at their proximal ends to electronic circuitry within the enclosure. The pins extend through the feedthru assembly to a point outside the enclosure, where they may be electrically coupled to electronic circuitry of another device.

Reliable connections between feedthru pins and electronics housed within an enclosure are often difficult to achieve when there are many connections to be made and/or when the enclosure is relatively small. With advancements in technology, many implantable devices have become increasingly complex and smaller in size. Hence, it is becoming increasingly difficult to make reliable connections between feedthru pins and electronics within an enclosure of an implantable device.

SUMMARY

A feedthru assembly configured to provide a conductive path extending between an interior of an enclosure and an exterior of the enclosure includes a flange, at least one conductive pin, and at least one insulative member. The flange is configured to couple to the enclosure and has one or more holes therein. The at least one conductive pin includes a hollow lumen extending therethrough and is configured to extend through the at least one or more holes of the flange such that a proximal end of the at least one pin is in communication with the interior of the enclosure and a distal end of the at least one pin is in communication with the exterior of the enclosure. The at least one insulative member is configured to prevent the at least one pin from making physical contact with the flange.

Methods of making a feedthru assembly configured to provide a conductive path extending between an interior of an enclosure and an exterior of the enclosure include providing at least one conductive pin having a hollow lumen extending therethrough, at least partially surrounding an outer surface of the pin with at least one insulative member, and coupling an outside surface of the at least one insulative member to a flange. The flange is coupled to the enclosure such that a proximal end of the at least one pin is in communication with the interior of the enclosure and a distal end of the at least one pin is in communication with the exterior of the enclosure.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

A feedthru assembly and methods of making the same are described herein. The feedthru assembly is configured to provide a conductive path extending between an interior of an enclosure and an exterior of the enclosure and includes a flange, at least one conductive pin, and at least one insulative member. The flange is configured to couple to the enclosure and has one or more holes therein. The at least one conductive pin includes a hollow lumen extending therethrough and is configured to extend through the at least one or more holes of the flange such that a proximal end of the at least one pin is in communication with the interior of the enclosure and a distal end of the at least one pin is in communication with the exterior of the enclosure. The at least one insulative member is configured to prevent the at least one pin from making physical contact with the flange.

As will be described in more detail below, the feedthru assembly described herein facilitates the connection of electronic circuitry that is to be disposed within the enclosure to one or more of the conductive pins. For example, one or more conductive wires may be connected at their proximal ends to electronic circuitry that has not yet been inserted into the enclosure. The distal end of the wires may then be guided through the hollow lumens of the pins and pulled until the electronic circuitry is properly disposed within the enclosure. The wire may then be trimmed and hermetically sealed or otherwise coupled to the pin. In this manner, a conductive path may be established between the electronic circuitry within the enclosure and an electronic component located outside the enclosure.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

As used herein and in the appended claims, the terms "implantable medical device," "implanted device" and variations thereof will be used broadly to refer to any type of device that is implanted within a patient to perform any function. For example, the implantable device may be, but is not limited to, a stimulator, pacemaker, or defibrillator.

It will be recognized that the feedthru assemblies described herein may be used with any device configured to be electrically coupled to another device and are not limited to use with implantable devices only. For example, the feedthru assemblies described herein may be used with computers, computer accessories, electromechanical devices, or any other device. However, for illustrative purposes only, the feedthru assemblies described herein correspond to implantable devices.

Figure 1:
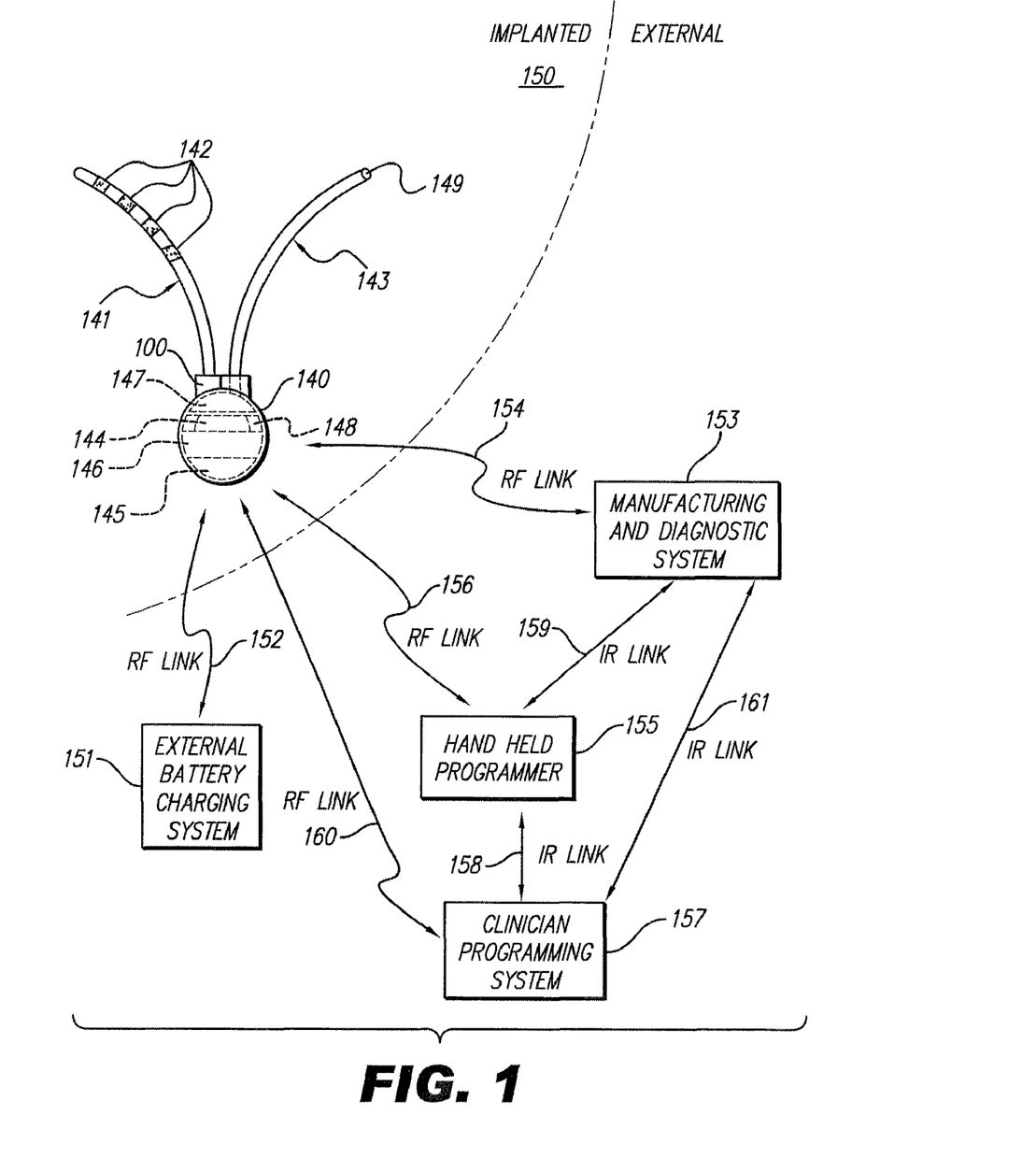
FIG. 1 illustrates an exemplary implantable stimulator according to principles described herein.

To facilitate an understanding of an exemplary implantable device with which the feedthru assemblies described herein may be used, an exemplary implantable stimulator will now be described in connection with FIG. 1. FIG. 1 illustrates an implantable stimulator (140) that may be implanted within a patient (150) and used to apply a stimulus to a stimulation site, e.g., an electrical stimulation of the stimulation site, an infusion of one or more drugs at the stimulation site, or both. The electrical stimulation function of the stimulator (140) will be described first, followed by an explanation of the possible drug delivery function of the stimulator (140). It will be understood, however, that the stimulator (140) may be configured to provide only electrical stimulation, only a drug stimulation, both types of stimulation or any other type of stimulation as best suits a particular patient.

The exemplary stimulator (140) shown in FIG. 1 is configured to provide electrical stimulation to a stimulation site via a lead (141) having a number of electrodes (142) disposed thereon. The lead (141) may include any number of electrodes (142) as best serves a particular application. The electrodes (142) may be arranged as an array, for example, having at least two or at least four collinear electrodes. In some examples, the electrodes are alternatively inductively coupled to the stimulator (140). The lead (141) may be thin (e.g., less than 3 millimeters in diameter) such that the lead (141) may be positioned near a stimulation site. In some alternative examples, the stimulator (140) is leadless.

As shown in FIG. 1, the stimulator (140) may include a feedthru assembly (100). The feedthru assembly (100) may include a number of pins configured to electrically connect the circuitry within the stimulator (140) to the lead (141) and/or to any other device. The feedthru assembly (100) will be described in more detail below.

As illustrated in FIG. 1, the stimulator (140) includes a number of components. It will be recognized that the stimulator (140) may include additional or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link or a wire connection. One type of rechargeable battery that may be used is described in U.S. Pat. No. 6,596,439, which is incorporated herein by reference in its entirety. Other battery construction techniques that may be used to make a power source (145) include those shown, e.g., in U.S. Pat. Nos. 6,280,873; 6,458, 171; 6,605,383; and 6,607,843, all of which are incorporated herein by reference in their respective entireties. Recharging can be performed using an external charger.

The stimulator (140) may also include a coil (148) configured to receive and/or emit a magnetic field (also referred to as a radio frequency (RF) field) that is used to communicate with, or receive power from, one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). Additionally or alternatively, the EBCS (151) may provide power to the power source (145) via a direct wire link (not shown). External devices including, but not limited to, a hand held programmer (HHP) (155), clinician programming system (CPS) (157), and/or a manufacturing and diagnostic system (MDS) (153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into the stimulation site.

Additionally, if multiple external devices are used in the treatment of a patient, there may be some communication among those external devices, as well as with the implanted stimulator (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140) may alternatively or additionally be configured to produce multipolar stimulation including, but not limited to, bipolar or tripolar stimulation.

The electrical circuitry (144) may include one or more processors configured to decode stimulation parameters and generate the stimulation pulses. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation or vice versa. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different stimulation sites and/or different patients. Thus, in some embodiments, the stimulation parameters may be adjusted by the patient, a clinician, or other user of the stimulator (140) as best serves the particular stimulation site or patient being treated. The stimulation parameters may also be automatically adjusted by the stimulator (140), as will be described below. For example, the stimulator (140) may increase excitement of a stimulation site, for example, by applying a stimulation current having a relatively low frequency (e.g., less than 100 Hz). The stimulator (140) may also decrease excitement of a stimulation site by applying a relatively high frequency (e.g., greater than 100 Hz). The stimulator (140) may also, or alternatively, be programmed to apply the stimulation current to a stimulation site intermittently or continuously.

Additionally, the exemplary stimulator (140) shown in FIG. 1 is configured to apply one or more drugs at a stimulation site within a patient. For this purpose, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at the stimulation site. In some embodiments, the stimulator (140) may include multiple catheters (143) and/or pumps (147) for storing and infusing dosages of the one or more drugs at the stimulation site.

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

In some embodiments, the one or more drugs are infused chronically into the stimulation site. Additionally or alternatively, the one or more drugs may be infused acutely into the stimulation site in response to a biological signal or a sensed need for the one or more drugs.

The stimulator (140) of FIG. 1 is illustrative of many types of stimulators that may be used to apply a stimulus to a stimulation site. For example, the stimulator (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus at a stimulation site within a patient. Exemplary IPGs suitable for use as described herein include, but are not limited to, those disclosed in U.S. Pat. Nos. 6,381,496; 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary cochlear implants suitable for use as described herein include, but are not limited to, those disclosed in U.S. Pat. Nos. 6,219,580; 6,272,382; and 6,308,101. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

Alternatively, the stimulator (140) may include an implantable microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017 and in U.S. Patent Publication No. 20040059392. All of these listed patents and publication are incorporated herein by reference in their respective entireties.

Some or all of the components of the stimulator (140) described above may be housed within a hermetically sealed enclosure configured to exclude water vapor but permit passage of electromagnetic fields used to transmit data and/or power. In some examples, the enclosure may be composed of biocompatible materials such as, but not limited to, glass, ceramic, metal, or any other material that provides a hermetic package.

Figure 2:
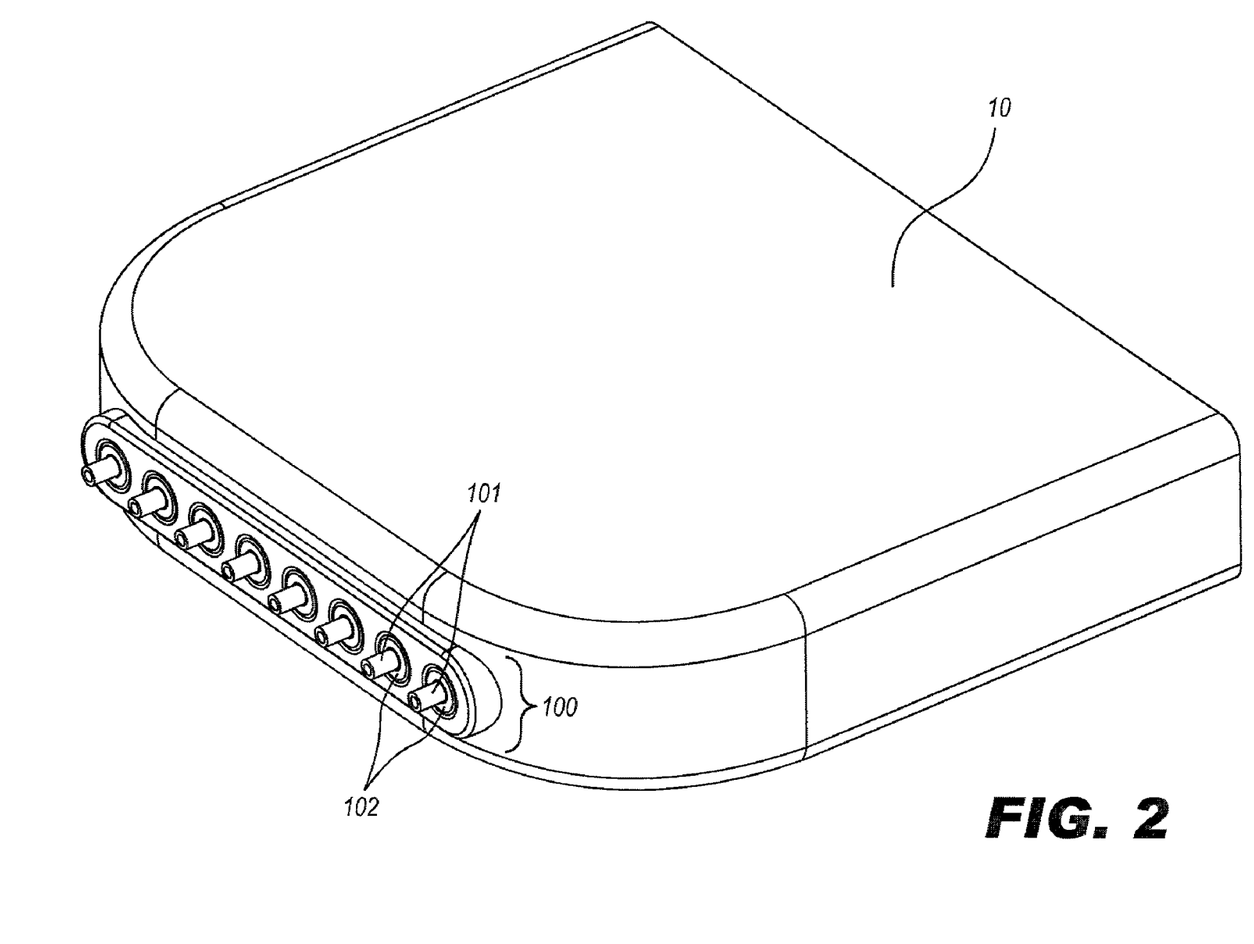
FIG. 2 is a perspective view of an exemplary enclosure having a feedthru assembly disposed at one of its ends according to principles described herein.

FIG. 2 is a perspective view of an exemplary enclosure (10) having a feedthru assembly (100) disposed at one of its ends. In some examples, the enclosure (10) houses one or more components of an implantable device (e.g., stimulator (140)). Alternatively, the enclosure (10) may house one or more components of any other type of device as best serves a particular application. For illustrative purposes only, it will be assumed in the examples given herein that the enclosure (10) is hermetically sealed. However, it will be recognized that the enclosure (10) may not be hermetically sealed in some applications.

As shown in FIG. 2, the feedthru assembly (100) may include any number of spaced pins (101) as best serves a particular application. Each pin (101) may be electrically coupled to electronic circuitry located within the enclosure (10) and may be made out of any suitable conductive metal. The feedthru assembly (100) may also include a number of insulative tubes (102) configured to hold the pins (101) in place and prevent aberrant electrical contact between the pins (101) and/or electrical circuitry within the device (10). The pins (101) and insulative tubes (102) will be described in more detail below.

As mentioned, it is often difficult to connect each of the pins (101) to electronic circuitry within an enclosure (10) that is relatively small, such as one that may be used to the house electronic circuitry of an implantable device. Hence, as will be described in FIGS. 3-6, to facilitate the making of connections between the pins (101) of a feedthru assembly (100) and electronic circuitry within an enclosure (10), each pin (101) within the feedthru assembly (100) may include a hollow lumen (105) that extends along its entire length through which a conductive wire may be passed. The conductive wire may be connected at its proximal end to electronic circuitry that has not yet been inserted into the enclosure (10). The distal end of the wire may then be guided through the hollow lumen (105) of the pin (101) and pulled until the electronic circuitry is properly disposed within the enclosure (10). The wire may then be trimmed and hermetically sealed or otherwise coupled to the pin (101). In this manner, the feedthru assembly (100) facilitates more reliable connections between the pins (101) and electronic circuitry housed within the enclosure (10).

Figure 3:
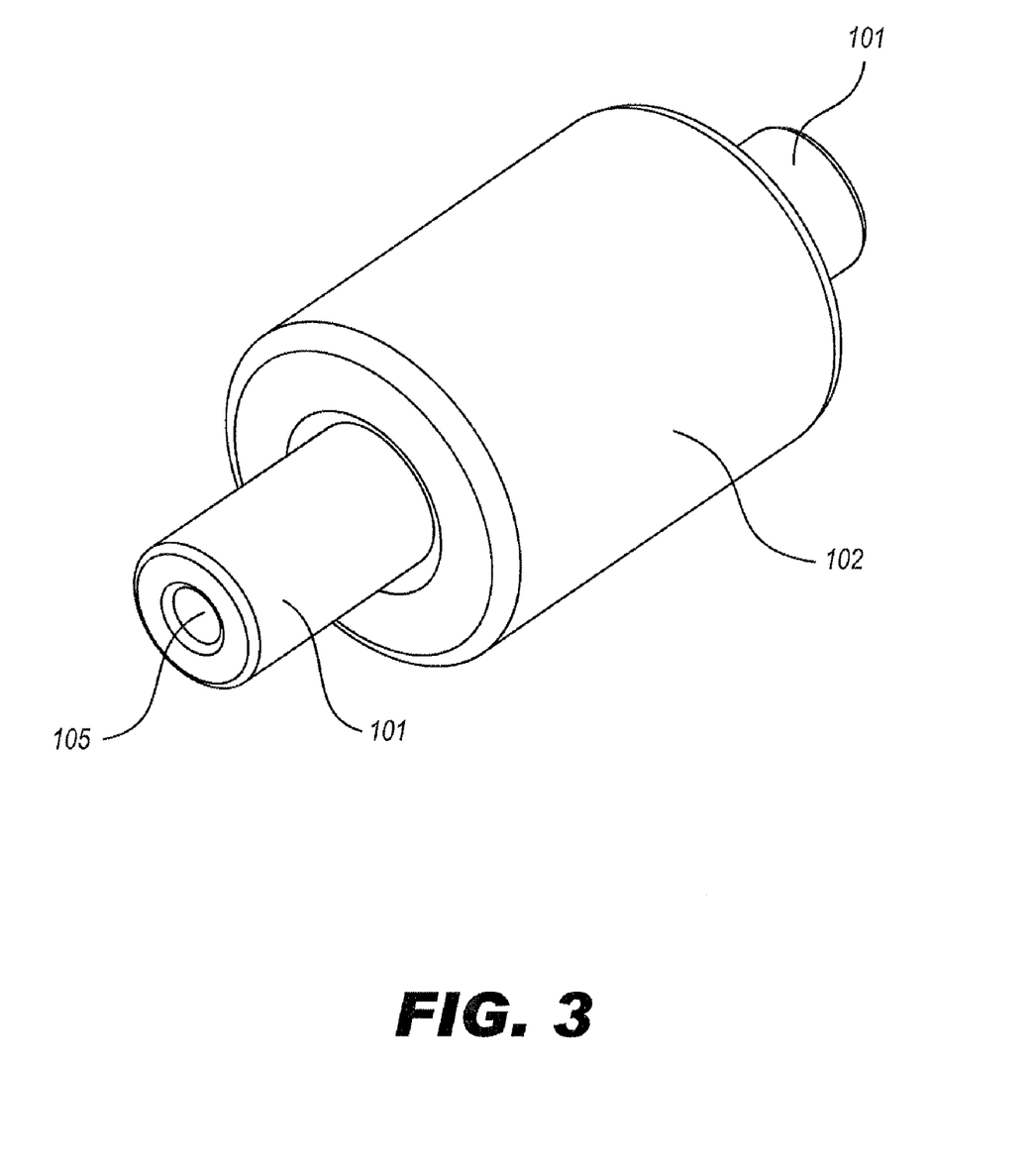
FIG. 3 is a perspective view of a conductive pin that has been hermetically coupled to an insulative tube according to principles described herein.

An exemplary method of making the feedthru assembly (100) will now be described in connection with FIGS. 3-6. Each conductive pin (101) may first be hermetically coupled to an insulative tube (102). For example, FIG. 3 is a perspective view of a conductive pin (101) that has been hermetically coupled to an insulative tube (102). Any suitable process (e.g., brazing, co-firing, laser welding, molding, and/or bonding with conductive epoxy) may be used to hermetically couple the pin (101) to the insulative tube (102).

The insulative tube (102) shown in FIG. 3 may be made out of any insulative material including, but not limited to, ceramic or glass, and is configured to surround at least an outer surface of the pin (101). The insulative tube (102) serves in part to prevent aberrant electrical contact between adjacent pins (101). As shown in FIG. 3, distal and proximal ends of the pin (101) may extend beyond the ends of the insulative tube (102). In this manner, the distal and/or proximal ends of the pin (101) may be connected to electronic circuitry, wires, leads, and/or any other conductive component.

Each pin (101) within the feedthru assembly (100; FIG. 2) may be made out of any suitable conductive material (e.g., platinum, iridium, tantalum, titanium, titanium nitride, niobium or alloys of any of these). As shown in FIG. 3, each pin (101) includes a hollow lumen (105) that extends along its entire length. It will be recognized that the pin (101) and/or lumen (105) may have any suitable size and shape. In some examples, the lumen (105) has a diameter that is slightly larger than that of a conductive wire that is to be passed therethrough.

Figure 4:
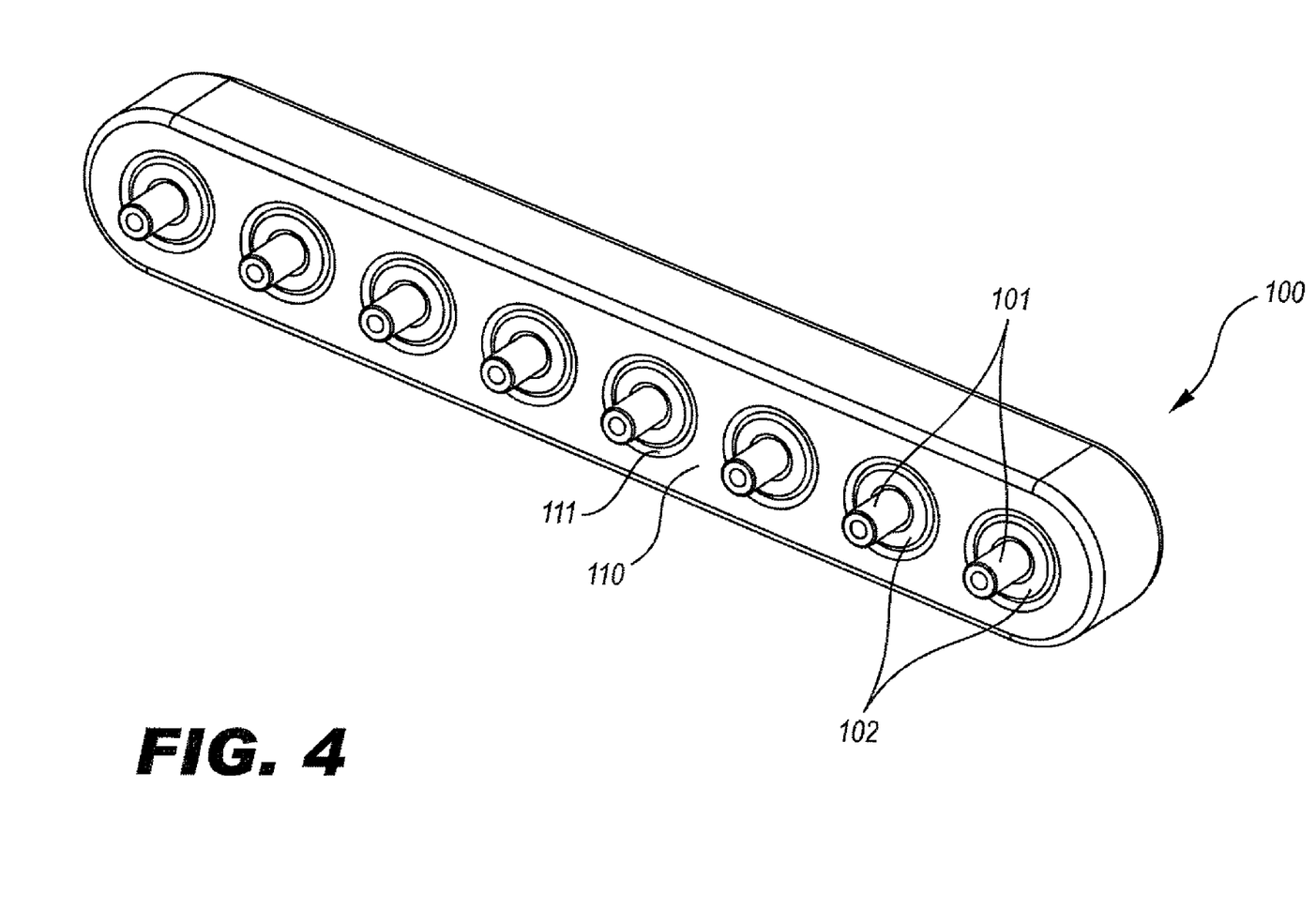
FIG. 4 is a perspective view of a feedthru assembly wherein a number of conductive pins are each surrounded by insulative tubes according to principles described herein.

Once each pin (101) has been coupled to an insulative tube (102), each insulative tube (102) is hermetically coupled to a flange to form the feedthru assembly (100). For example, FIG. 4 is a perspective view of a feedthru assembly (100) and shows a number of insulative tubes (102) that have been coupled to a metal flange (110). The flange (110) may be made out of metal or any other biocompatible material. In some examples, the flange (110) is made out of the same material as that of the enclosure (10; FIG. 2).

In some examples, the insulative tubes (102) are brazed, co-fired, or otherwise hermetically coupled to corresponding holes (111) that have been formed in the flange (110). As shown in FIG. 4, the pins (101) may extend out from the front surface of the flange (110). The pins (101) may additionally or alternatively extend out from the back surface of the flange (110). However, it will be recognized that the pins (101) may alternatively be flush with the surface of the flange (110) or recessed with respect to the surface of the flange (110) as best serves a particular application.

In some examples, the hermetic coupling of the pins (101) to the insulative tubes (102) and the insulative tubes (102) to the flange (110) may be performed simultaneously. Alternatively, the hermetic coupling may be performed in steps.

Figure 5:
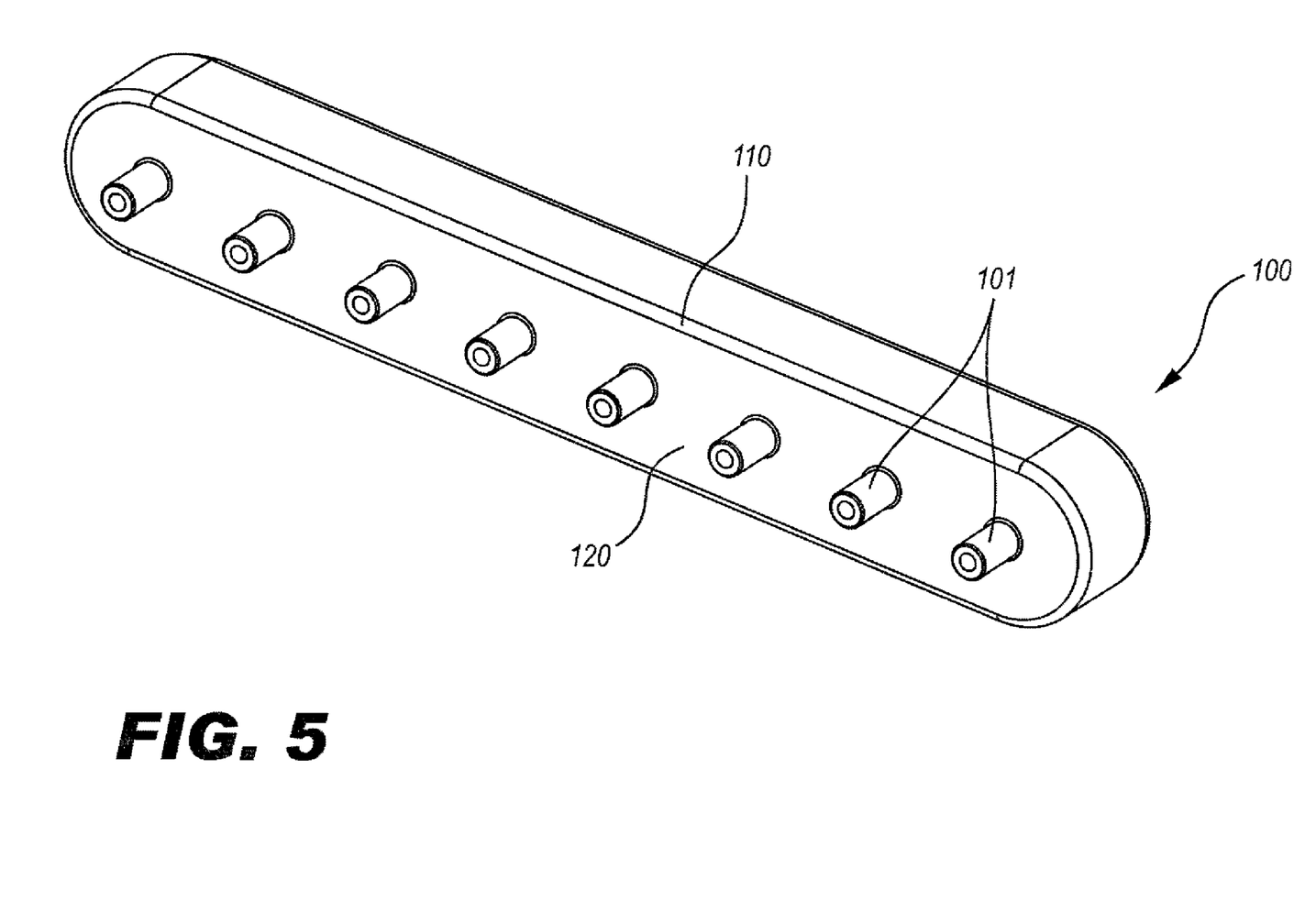
FIG. 5 is a perspective view of a feedthru assembly wherein each of the conductive pins is hermetically coupled to a single insulative plate according to principles described herein.

In some alternative examples, as shown in FIG. 5, each of the conductive pins (101) may be hermetically coupled to a single insulative plate (120) instead of to multiple insulative tubes (102; FIG. 4). The insulative plate (120) may be made out of any suitable insulative material including, but not limited to, ceramic or glass. The insulative plate (120) may then be coupled to the flange (110), as shown in FIG. 5. However, for illustrative purposes only, it will be assumed in the examples given herein that the pins (101) are hermetically coupled to individual insulative tubes (102; FIG. 4).

Figure 6:
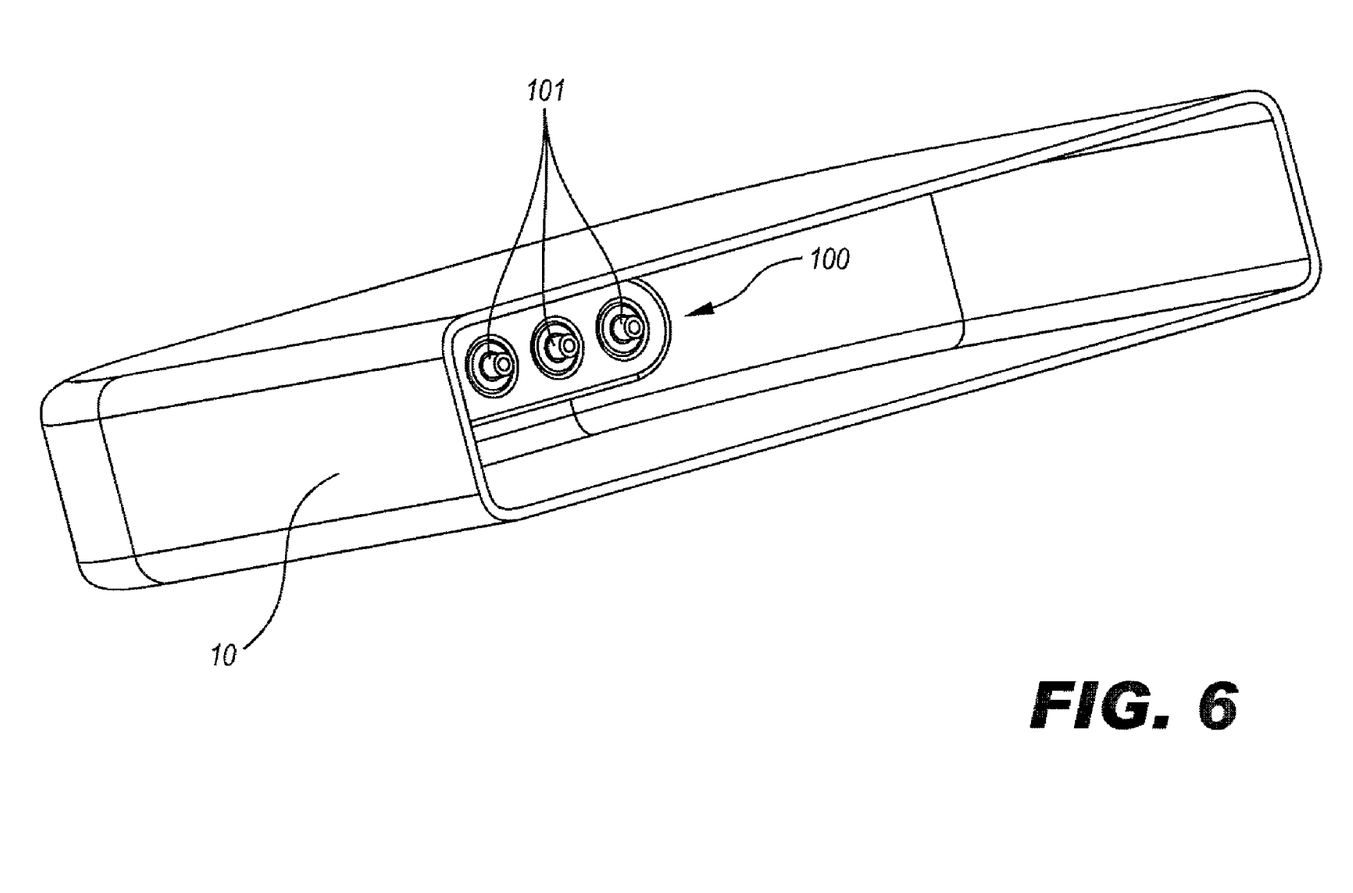
FIG. 6 is a perspective rear view of the enclosure with the feedthru assembly hermetically coupled thereto according to principles described herein.

After the insulative tubes (102; FIG. 4) are coupled to the flange (110), the feedthru assembly (100) may be hermetically coupled to the enclosure (10), as illustrated already in FIG. 2. The feedthru assembly (100) may be coupled to the enclosure (10) using any of a number of different coupling techniques including, but not limited to, brazing, co-firing, laser welding, molding, and/or bonding with conductive epoxy. FIG. 6 is a perspective rear view of the enclosure (10) with the feedthru assembly (100) hermetically coupled thereto. As shown in FIG. 6, one or more of the pins (101) may extend out from the feedthru assembly (100) towards the interior of the enclosure (10). In this manner, as will be described in more detail below, electronic circuitry that is to be disposed within the enclosure (10) may be electrically coupled to one or more of the pins (101).

It will be recognized that many alternative methods may be used to construct the feedthru assembly (100). For example, the feedthru assembly (100) may alternatively be made out of the same mold as the enclosure (10).

An exemplary method of electrically coupling one or more of the pins (101) to electronic circuitry that is to be disposed within the enclosure (10) will now be described in connection with FIGS. 7-10. It will be recognized that the steps described herein may be modified, reordered, added to, or removed as best serves a particular application.

Figure 7:
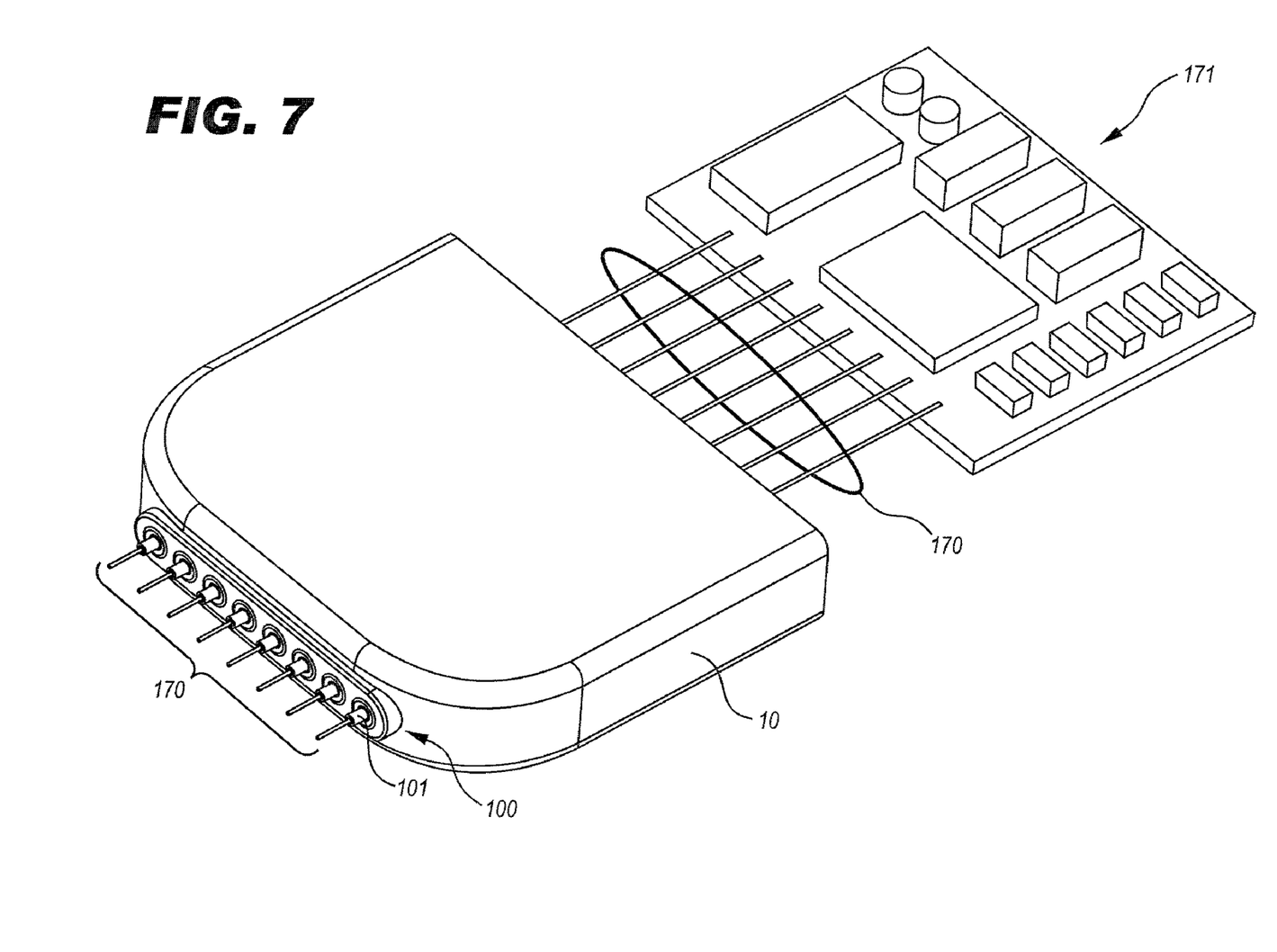
FIG. 7 shows one or more conductive wires coupled to electronic circuitry prior to the circuitry being inserted within the enclosure according to principles described herein.

As shown in FIG. 7, one or more conductive wires (170) may first be coupled to electronic circuitry (171) prior to the circuitry (171) being inserted within the enclosure (10). As shown in FIG. 7, the electronic circuitry (171) may include any number of components and may be disposed on a printed circuit board (PCB), for example. The wires (170) may be coupled to the electronic circuitry (171) using any suitable coupling technique including, but not limited to, welding, soldering, or bonding with conductive epoxy.

The wires (170) may then be guided or fed through the lumens of one or more of the pins (101). It will be recognized that the wires (170) may alternatively be guided through the lumens of one or more of the pins (101) prior to being coupled to the electronic circuitry (171).

Figure 8:
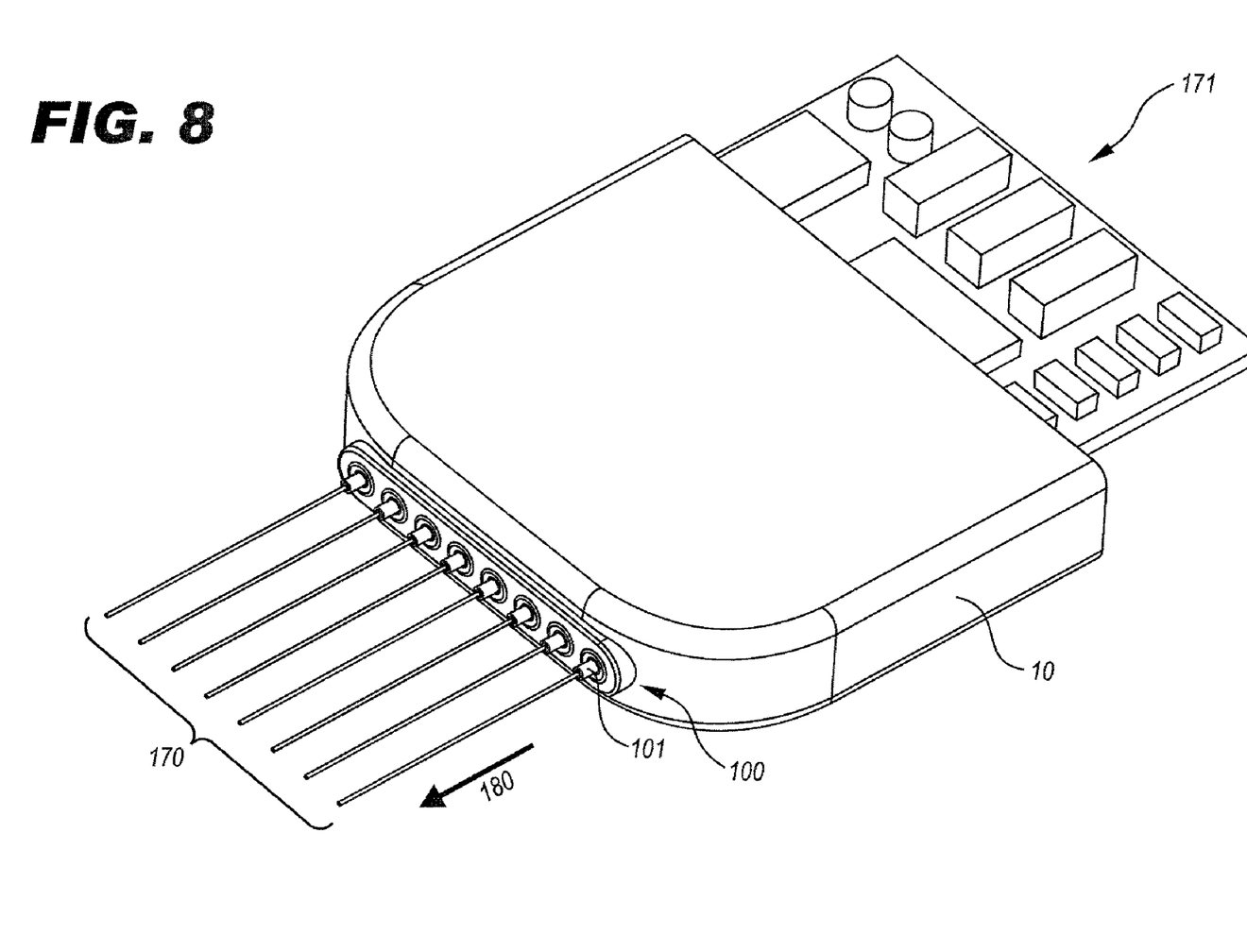
FIG. 8 shows that the wires of FIG. 7 may be pulled so as to insert the electronic circuitry into the enclosure according to principles described herein.

FIG. 8 shows that the wires (170) may then be pulled in the direction of the arrow (180) so as to insert the electronic circuitry (171) into the enclosure (10). In some examples, the interior surface(s) of the enclosure (10) may include one or more guide rails, grooves, recesses, or other securing devices configured to facilitate the insertion and securing of the electronic circuitry (171) within the enclosure (10).

Figure 9:
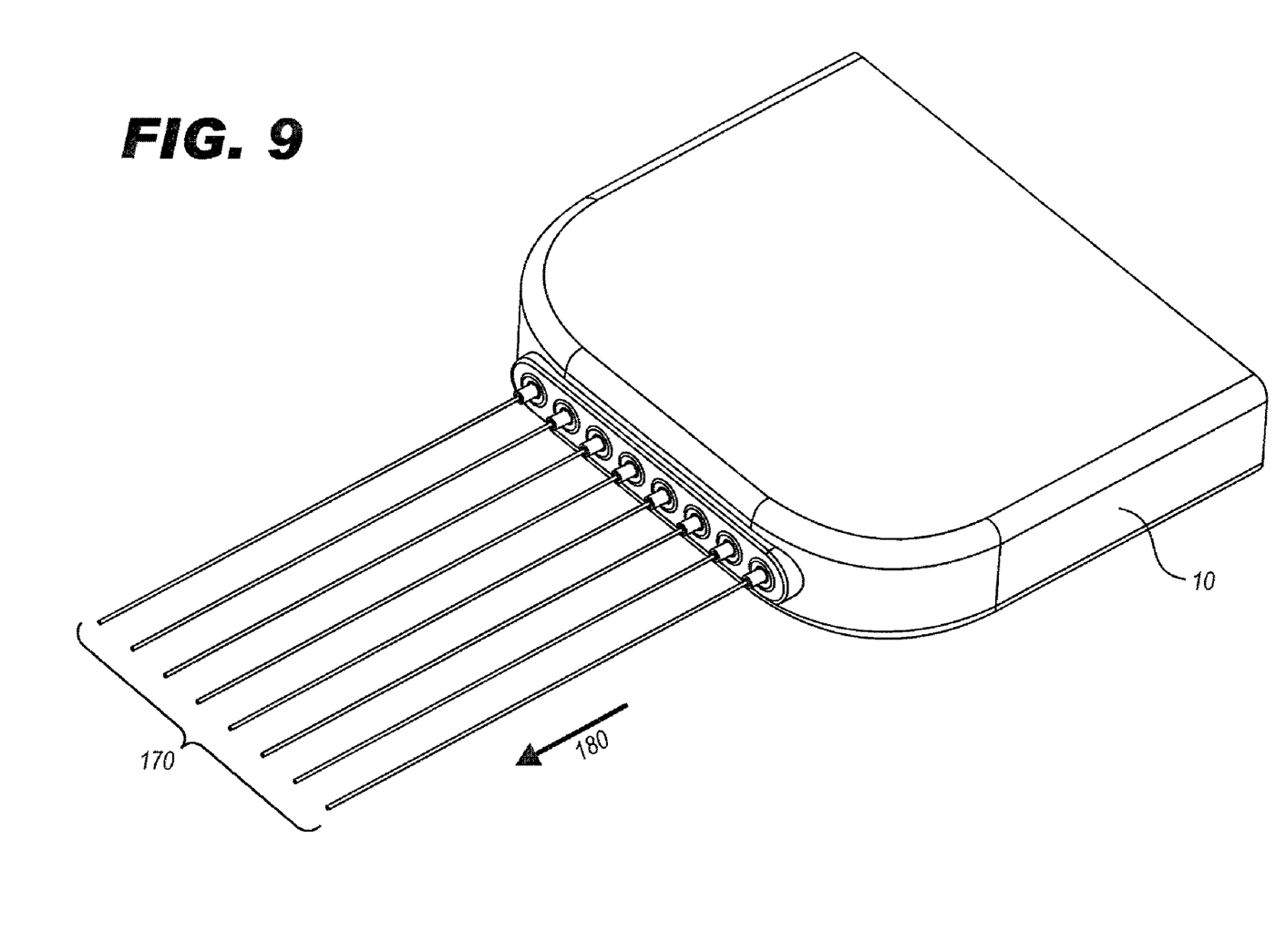
FIG. 9 is a perspective view of the enclosure wherein the wires have been sufficiently pulled such that the electronic circuitry is entirely disposed within the enclosure according to principles described herein.

FIG. 9 is a perspective view of the enclosure (10) wherein the wires (170) have been sufficiently pulled in the direction of the arrow (180) such that the electronic circuitry (171) is entirely disposed within the enclosure (10).

In some examples, test equipment and/or other devices may then be connected to the portion of the wires (170) located external to the enclosure (10) to test the connections with the electronic circuitry (171), the function of the electronic circuitry (171), and/or any other operations of the electronic circuitry (171). Once it has been determined that the electronic circuitry (171) is functioning properly, a backing (not shown) may be hermetically coupled to the enclosure (10) so as to hermetically seal the enclosure (10).

Figure 10:
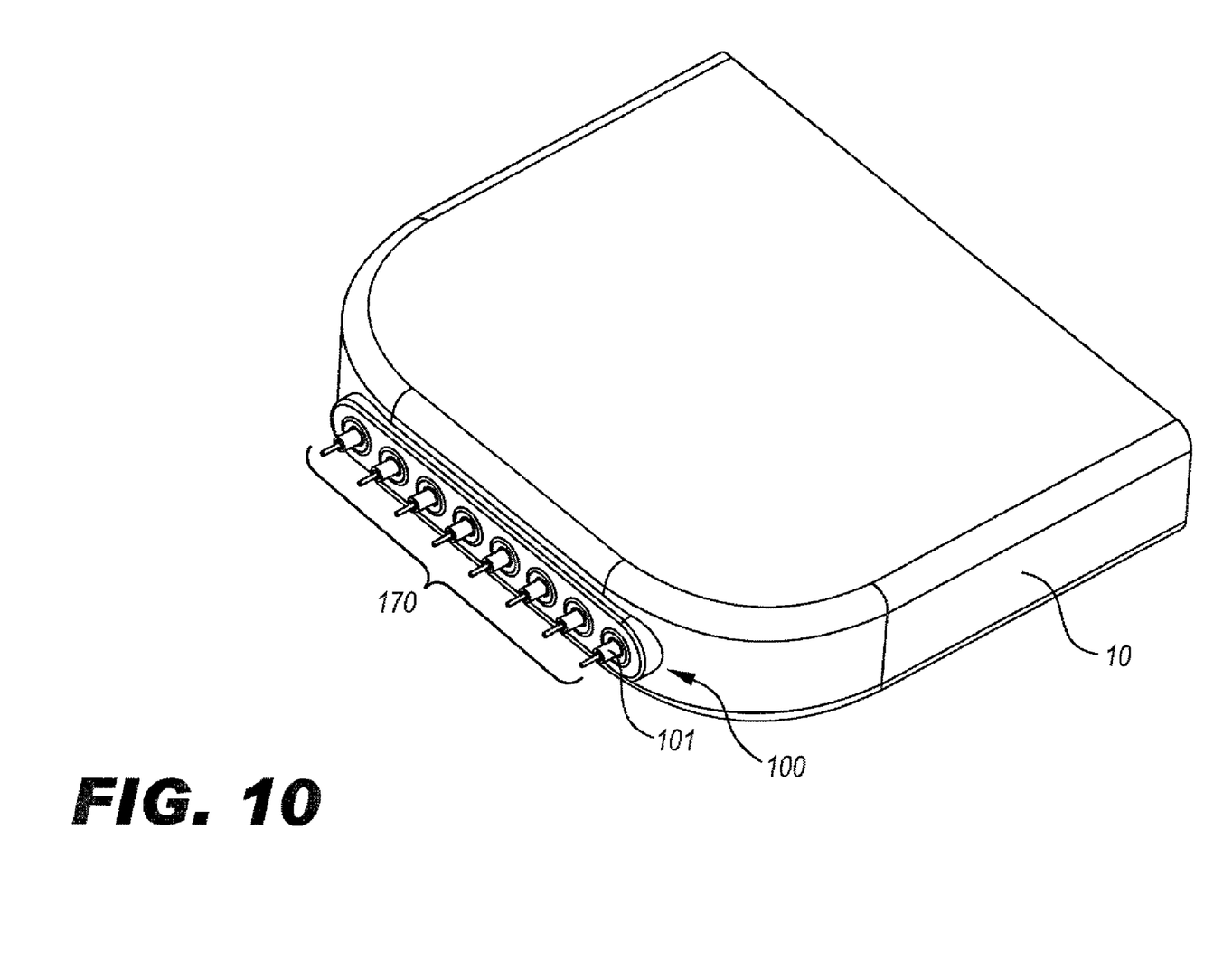
FIG. 10 is a perspective view of the enclosure wherein the wires have been trimmed to the distal end of the pins according to principles described herein.

Next, as shown in FIG. 10, the wires (170) may be trimmed to the distal end of the pins (101). The wires (170) may then be hermetically coupled to the pins (101) using any suitable technique. For example, the wires (170) may be laser welded, brazed, soldered, bonded with conductive epoxy, or otherwise hermetically coupled to the pins (101). The pins (101) may then be used to electrically couple the electronic circuitry within the enclosure (10) to one or more devices external to the enclosure (10).

Figure 11:
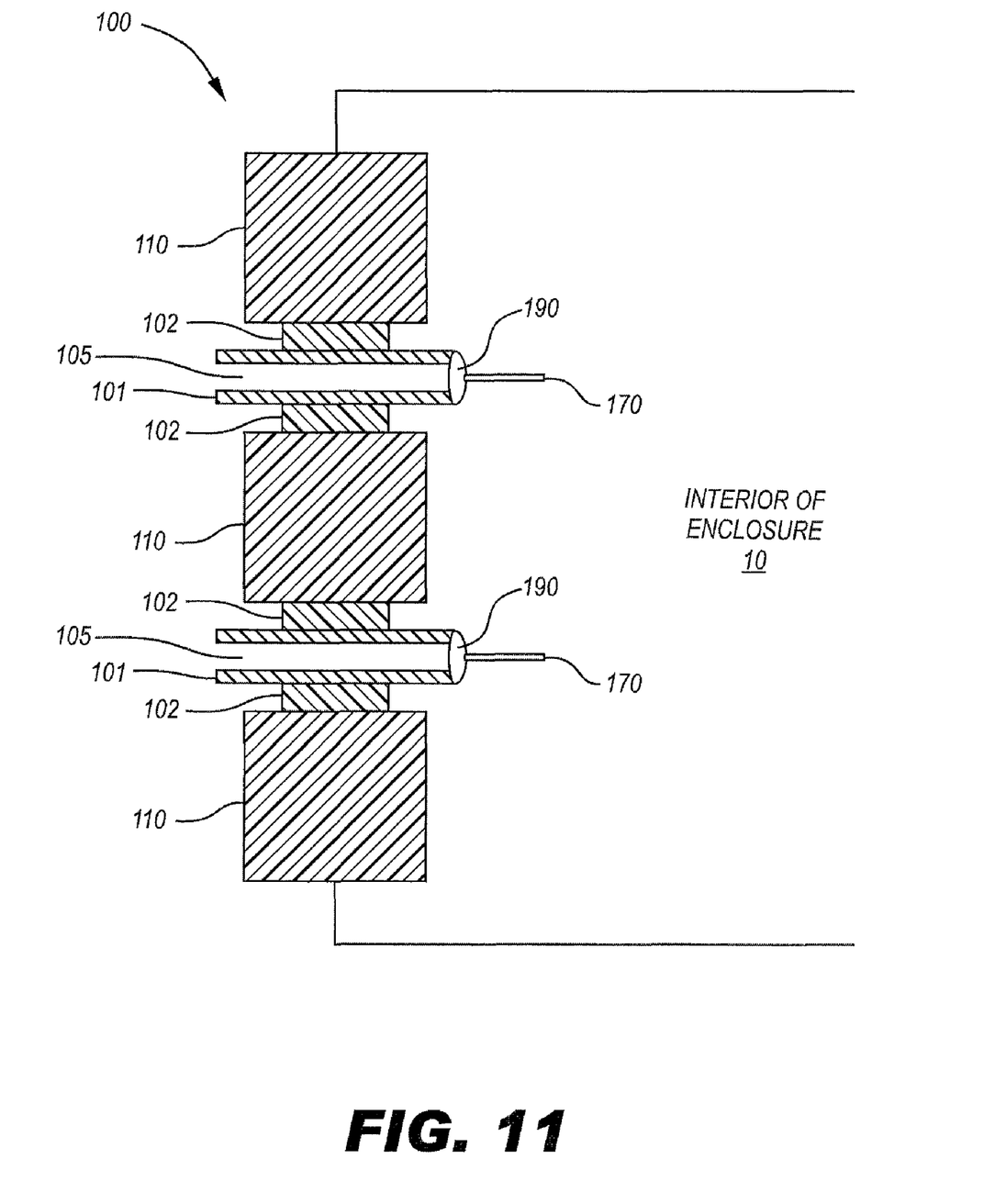
FIG. 11 is a cross-sectional side view of the feedthru assembly showing the pins as hermetically coupled to the wires within the interior of the enclosure according to principles described herein.

It will be recognized that a number of alternative methods of coupling the electrical circuitry (171) to the pins (101) may be used. For example, the pins (101) may first be hermetically coupled to the wires (170) within the interior of the enclosure (10). FIG. 11 is a cross-sectional side view of the feedthru assembly (100) showing the pins (101) as hermetically coupled to the wires (170) via a hermetic seal (190) within the interior of the enclosure (10). The hermetic seal (190) may be made using any suitable hermetic coupling technique including, but not limited to, brazing, co-firing, laser welding, molding, and/or bonding with conductive epoxy.

By hermetically coupling the pins (101) to the wires (170) within the interior of the enclosure (10), as shown in FIG. 11, the portion of the pins (101) external to the enclosure (10) may be left unsealed. In this manner, an external lead or wire may be connected to one of the pins (101) simply by inserting the lead or wire into the hollow lumen of the pin (101) and crimping or otherwise securing the lead or wire to the pin (101).

Figure 12:
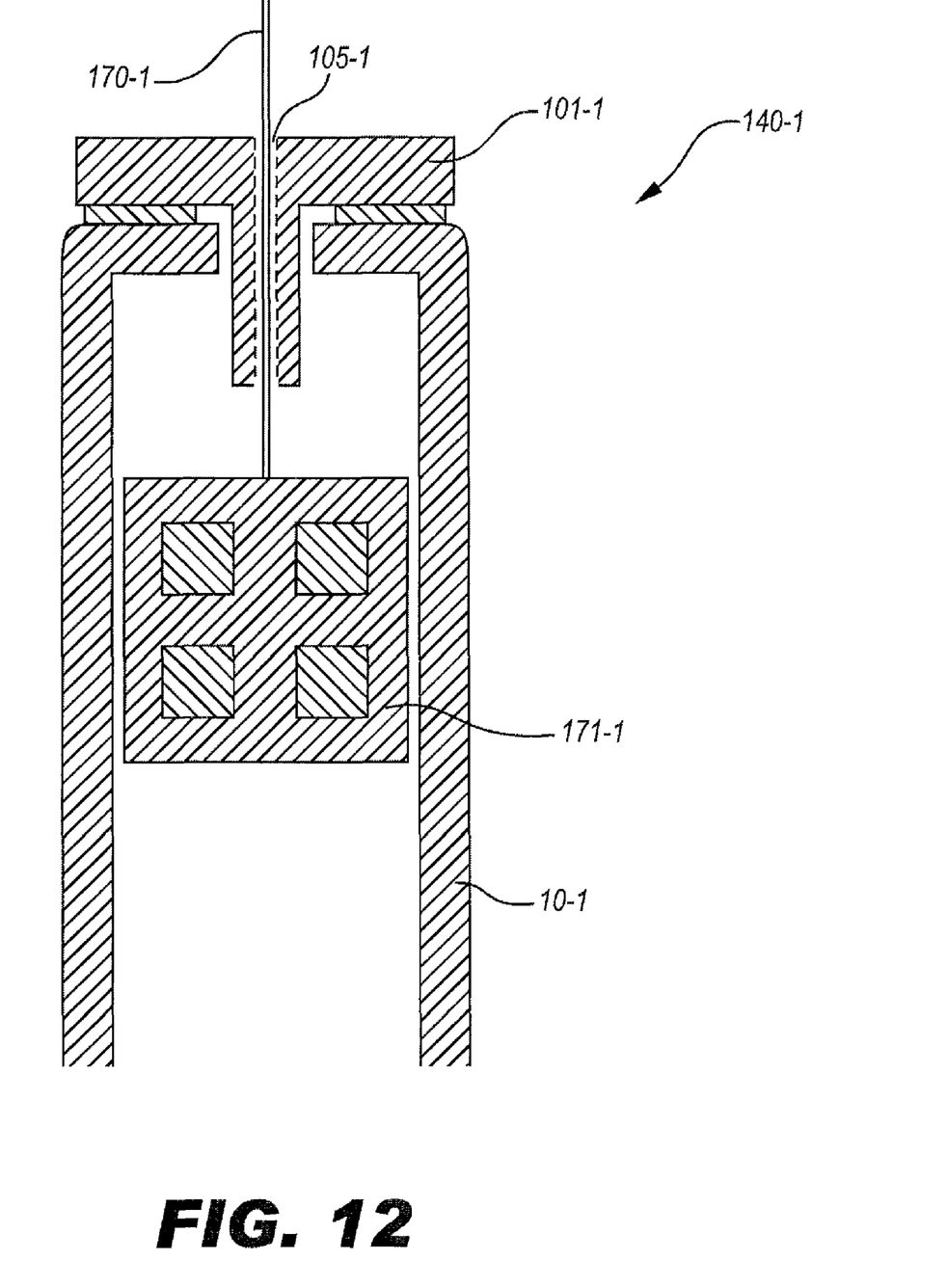
FIG. 12 is a cross-sectional side view of an exemplary stimulator that may be configured to have one or more electrodes disposed thereon according to principles described herein.

As mentioned, each of the pins (101) may have any suitable size and/or shape as best serves a particular application. In some examples, one or more pins (101) may serve as an electrode that is coupled to the surface of an implantable stimulator (e.g., stimulator (140)). For example, FIG. 12 is a cross-sectional side view of an exemplary stimulator (140-1) that may be configured to have one or more electrodes disposed thereon. As shown in FIG. 12, a pin (101-1) having a lumen (105-1) extending therethrough may be hermetically coupled to the surface of the enclosure (10-1) of the stimulator (140-1). A conductive wire (170-1) may be coupled to electronic circuitry (171-1) and then guided through the lumen (105-1) of the pin (101-1). As described above, the wire (170-1) may be pulled away from the enclosure (10-1) of the stimulator (140-1) to insert the electronic circuitry (171-1) into the enclosure (10-1). The wire (170-1) may then be trimmed and hermetically coupled to the pin (101-1).

The preceding description has been presented only to illustrate and describe embodiments of the invention. It is not intended to be exhaustive or to limit the invention to any precise form disclosed. Many modifications and variations are possible in light of the above teaching.

What is claimed is:

1. A device comprising:
   an enclosure having an interior and an exterior; and
   a feedthru assembly configured to provide a conductive path extending between the interior of the enclosure and the exterior of said enclosure, comprising:
      a plurality of pins, each having a distal end and a proximal end such that the proximal end of each pin is in communication with the interior of the enclosure and the distal end of each pin is in communication with the exterior of the enclosure, wherein the pins are configured and arranged for electrically coupling electronic circuitry within the interior of the enclosure to a lead exterior of the enclosure, each pin comprising a hollow lumen for receiving a conductive wire;

an insulative member coupled to the pins to prevent electrical contact between said pins; and a plurality of conductive wires, each conductive wire passing completely through the hollow lumen of one of the pins.

2. The device of claim 1, wherein said pins are made out of a conductive material.

3. The device of claim 1, wherein said insulative member is an insulative tube having a proximal end and a distal end.

4. The device of claim 1, wherein said insulative member is an insulative plate.

5. The device of claim 1, wherein said pins are hermetically coupled to said insulative member.

6. The device of claim 1, wherein said hollow lumen extends along the entire length of the pin.

7. The device of claim 1, wherein said insulative member is made out of ceramic.

8. The device of claim 1, wherein said insulative member is made out of glass.

9. The device of claim 3, wherein the distal and proximal ends of each pin extend beyond the distal and proximal ends of the insulative tube.

10. The device of claim 3, wherein an end of each pin extends beyond an end of the insulative tube.

11. The device of claim 1, wherein the lumen has a diameter that is slightly larger than that of the conductive wire that passes therethrough.

12. The device of claim 1, wherein the plurality of pins are configured to serve as electrodes.

13. The device of claim 1, wherein said device is an implantable pulse generator.

14. The device of claim 1, further comprising a lead configured and arranged for removably coupling to the implantable pulse generator.

15. A method of making a device comprising:

providing an enclosure having an interior and an exterior;

providing a plurality of pins, each having a distal end and a proximal end such that the proximal end of each pin is in communication with the interior of the enclosure and the distal end of each pin is in communication with the exterior of the enclosure, wherein the pins are configured and arranged for electrically coupling electronic circuitry within the interior of the enclosure to electronic circuitry exterior of the enclosure, each pin comprising a hollow lumen for receiving a conductive wire;

coupling an insulative member to the pins to prevent electrical contact between said pins; and guiding each of a plurality of conductive wires completely through the hollow lumen of a corresponding one of the pins.

16. The method of claim 15, wherein guiding each of a plurality of conductive wires comprises facilitating a passage of the conductive wires through the hollow lumens of the pins using a guiding element.

17. The method of claim 15, wherein coupling an insulative member comprises coupling at least one of the pins to an insulative tube, said insulative tube being configured to surround a portion of an outer surface of said at least one of the pins.

18. The method of claim 15, wherein coupling an insulative member comprises coupling the pins to an insulative plate.

19. The method of claim 15, wherein providing an enclosure comprises providing an enclosure housing electronic circuitry within the enclosure corresponding to an implantable medical device.

20. The method of claim 19, wherein the electronic circuitry corresponds to an implantable pulse generator.

* * * * *